United States Patent
Browse et al.

(10) Patent No.: US 6,194,167 B1
(45) Date of Patent: Feb. 27, 2001

(54) ω-3 FATTY ACID DESATURASE

(75) Inventors: John A. Browse, Palouse, WA (US); James P. Spychalla, Antigo, WI (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/025,578

(22) Filed: Feb. 18, 1998

Related U.S. Application Data

(60) Provisional application No. 60/038,409, filed on Feb. 18, 1997.

(51) Int. Cl.[7] .............................. C12N 5/04; C12N 15/09
(52) U.S. Cl. .................. 435/69.1; 435/419; 435/440; 435/252.3; 435/468; 800/281
(58) Field of Search ..................................... 800/281, 298; 435/69.1, 71.1, 440, 468, 471, 410, 419, 252.3, 254.2

(56) References Cited

PUBLICATIONS

L41807, http://www.ncbi.nlm.nih.gov:80, 1995.
D26019, http://www.ncbi.nlm.nih.gov:80, 1993.
L22931, http://www.ncbi.nlm.nih.gov:80, 1993.
L26296, http://www.ncbi.nlm.nih.gov:80, 1994.
M88884, http://www.ncbi.nlm.nih.gov:80, 1992.
U09503, http://www.ncbi.nlm.nih.gov:80, 1994.
Z14543, http://ww.ncbi.nlm.nih.gov:80, 1992.
Z14935, http://www.ncbi.nlm.nih.gov:80, 1992.
Arondel et al., "Map–Based Cloning of a Gene Controlling Omega–3 Fatty Acid Desaturation in Arabidopsis, " *Science* 258:1353–1355 (1992).
Browse, Glycerolipid Synthesis: Biochemistry and Regulation *Annu. Rev. Plant Physiol. Plant Mol. Biol.* 42:467–506 (1991).
Browse et al., in Arabidopsis, Meyerowitz et al. (ed.), Cold Spring Harbor Laboratory Press, New York, NY (1994).
Browse et al., "Mutants of Arabidopsis Deficient in the Synthesis of α–Linolenate," *J. Biol. Chem.* 268:16345–16351 (1993).
Grayburn et al., "Fatty Acid Alteration by a Δ9 Desaturase in Transgenic Tobacco Tissue," *Bio/Tech.* 10:675–677 (1992).
Jackson et al., "Identification of a Consensus Motif for Retention of Transmembrane Proteins in the Endoplasmic Reticulum," *EMBO J.* 9:3153–3162 (1990).
McConn et al., "The Critical Requirement for Linolenic Acid is Pollen Development, Not Photosynthesis, in an Arbidopsis Mutant," *Plant Cell* 8:403–416 (1996).
Miquel et al., "Arabidopsis Mutants Deficient in Poly–unsaturated Fatty Acid Synthesis," *J. Biol. Chem.* 267:1502–1509 (1992).
Okuley et al., "Arabidopsis FAD2 Gene Encodes the Enzyme that is Essential for Polyunsaturated Lipid Synthesis," *Plant Cell* 6:147–158 (1994).
Polashock et al., "Expression of the Yeast Δ–9 Fatty Acid Desaturase in *Nicotiana tabacum*, " *Plant Physiol.* 100:894–902 (1992).
Shanklin et al., "Eight Histidine Residues are Catalytically Essential in a Membrane–Associated Iron Enzyme, Stearoyl–CoA Desaturase, and Are Conserved in Alkane Hydroxylase and Xylene Monooxygenase, " *Biochem.* 33:12787–12794 (1994).
Stukey et al., "The OLE1 Gene of *Saccharomyces cerevisiae* Encodes the Δ9 Fatty Acid Desaturase and Can Be Functionally Replaced by the Rat Stearoyl–CoA Desaturase Gene, " *J. Biol. Chem* 265:20144–20149 (1990).
Yadav et al., "Cloning of Higher Plant ω–3 Fatty Acid Desaturases, " *Plant Physiol.* 103:467–476 (1993).
Yadav et al., in Biochemistry and Molecular Biology of Membrane and Storage Lipids of Plants, N. Murala and CR Somerville, eds., The American Society of Plant Physiologists (1993).
Bouchez et al., "A Binary Vector Based on Basta Resistance for In Planta Transformation of *Arabidopsis thaliana*, "*Life Sciences* 316:1188–1193 (1993).
Dellaporta et al., "A Plant DNA Minipreparation: Version II, " *Plant Mol. Biol. Rep.* 1:19–21 (1983).
Spychalla et al., "Agrobacterium–Mediated Transformation of Potato Stem and Tuber Tissue, Regeneration and PCR Screening for Transformation, " *Plant Tissue Culture Manual B11*:1–18 (1993).

*Primary Examiner*—Elizabeth F. McElwain
(74) *Attorney, Agent, or Firm*—Klarquist Sparkman Campbell Leigh & Whinston, LLP

(57) ABSTRACT

Recombinant expression of fat-1 gene of *Caenorhabditis elegans* in a wide variety of cells, including cells of *Arabidopsis thaliana* and *Saccharomyces cerevisiae*, produces a polypeptide having ω-3 desaturase activity.

4 Claims, 2 Drawing Sheets

```
CAAGTTTGAG GT                                                              12

ATG GTC GCT CAT TCC TCA GAA GGG TTA TCC GCC ACG GCT CCG GTC                57
Met Val Ala His Ser Ser Glu Gly Leu Ser Ala Thr Ala Pro Val
                  5              10                  15

ACC GGC GGA GAT GTT CTG GTT GAT GCT CGT GCA TCT CTT GAA GAA               102
Thr Gly Gly Asp Val Leu Val Asp Ala Arg Ala Ser Leu Glu Glu
                 20              25                  30

AAG GAG GCT CCA CGT GAT GTG AAT GCA AAC ACT AAA CAG GCC ACC               147
Lys Glu Ala Pro Arg Asp Val Asn Ala Asn Thr Lys Gln Ala Thr
                 35              40                  45

ACT GAA GAG CCA CGC ATC CAA TTA CCA ACT GTG GAT GCT TTC CGT               192
Thr Glu Glu Pro Arg Ile Gln Leu Pro Thr Val Asp Ala Phe Arg
                 50              55                  60

CGT GCA ATT CCA GCA CAC TGT TTC GAA AGA GAT CTC GTT AAA TCA               237
Arg Ala Ile Pro Ala His Cys Phe Glu Arg Asp Leu Val Lys Ser
                 65              70                  75

ATC AGA TAT TTG GTG CAA GAC TTT GCG GCA CTC ACA ATT CTC TAC               282
Ile Arg Tyr Leu Val Gln Asp Phe Ala Ala Leu Thr Ile Leu Tyr
                 80              85                  90

TTT GCT CTT CCA GCT TTT GAG TAC TTT GGA TTG TTT GGT TAC TTG               327
Phe Ala Leu Pro Ala Phe Glu Tyr Phe Gly Leu Phe Gly Tyr Leu
                 95             100                 105

GTT TGG AAC ATT TTT ATG GGA GTT TTT GGA TTC GCG TTG TTC GTC               372
Val Trp Asn Ile Phe Met Gly Val Phe Gly Phe Ala Leu Phe Val
                110             115                 120

GTT GGA CAC GAT TGT CTT CAT GGA TCA TTC TCT GAT AAT CAG AAT               417
Val Gly His Asp Cys Leu His Gly Ser Phe Ser Asp Asn Gln Asn
                125             130                 135

CTC AAT GAT TTC ATT GGA CAT ATC GCC TTC TCA CCA CTC TTC TCT               462
Leu Asn Asp Phe Ile Gly His Ile Ala Phe Ser Pro Leu Phe Ser
                140             145                 150

CCA TAC TTC CCA TGG CAG AAA AGT CAC AAG CTT CAC CAT GCT TTC               507
Pro Tyr Phe Pro Trp Gln Lys Ser His Lys Leu His His Ala Phe
                155             160                 165

ACC AAC CAC ATT GAC AAA GAT CAT GGA CAC GTG TGG ATT CAG GAT               552
Thr Asn His Ile Asp Lys Asp His Gly His Val Trp Ile Gln Asp
                170             175                 180

AAG GAT TGG GAA GCA ATG CCA TCA TGG AAA AGA TGG TTC AAT CCA               597
Lys Asp Trp Glu Ala Met Pro Ser Trp Lys Arg Trp Phe Asn Pro
                185             190                 195

ATT CCA TTC TCT GGA TGG CTT AAA TGG TTC CCA GTG TAC ACT TTA               642
Ile Pro Phe Ser Gly Trp Leu Lys Trp Phe Pro Val Tyr Thr Leu
                200             205                 210

TTC GGT TTC TGT GAT GGA TCT CAC TTC TGG CCA TAC TCT TCA CTT               687
```

FIG 1A

```
                Phe Gly Phe Cys Asp Gly Ser His Phe Trp Pro Tyr Ser Ser Leu
                            215                 220                 225

TTT GTT CGT AAC TCT GAC CGT GTT CAA TGT GTA ATC TCT GGA ATC                      732
Phe Val Arg Asn Ser Asp Arg Val Gln Cys Val Ile Ser Gly Ile
                230                 235                 240

TGT TGC TGT GTG TGT GCA TAT ATT GCT CTA ACA ATT GCT GGA TCA                      777
Cys Cys Cys Val Cys Ala Tyr Ile Ala Leu Thr Ile Ala Gly Ser
                245                 250                 255

TAT TCC AAT TGG TTC TGG TAC TAT TGG GTT CCA CTT TCT TTC TTC                      822
Tyr Ser Asn Trp Phe Trp Tyr Tyr Trp Val Pro Leu Ser Phe Phe
                260                 265                 270

GGA TTG ATG CTC GTC ATT GTT ACC TAT TTG CAA CAT GTC GAT GAT                      867
Gly Leu Met Leu Val Ile Val Thr Tyr Leu Gln His Val Asp Asp
                275                 280                 285

GTC GCT GAG GTG TAC GAG GCT GAT GAA TGG AGC TTC GTC CGT GGA                      912
Val Ala Glu Val Tyr Glu Ala Asp Glu Trp Ser Phe Val Arg Gly
                290                 295                 300

CAA ACC CAA ACC ATC GAT CGT TAC TAT GGA CTC GGA TTG GAC ACA                      957
Gln Thr Gln Thr Ile Asp Arg Tyr Tyr Gly Leu Gly Leu Asp Thr
                305                 310                 315

ACG ATG CAC CAT ATC ACA GAC GGA CAC GTT GCC CAT CAC TTC TTC                     1002
Thr Met His His Ile Thr Asp Gly His Val Ala His His Phe Phe
                320                 325                 330

AAC AAA ATC CCA CAT TAC CAT CTC ATC GAA GCA ACC GAA GGT GTC                     1047
Asn Lys Ile Pro His Tyr His Leu Ile Glu Ala Thr Glu Gly Val
                335                 340                 345

AAA AAG GTC TTG GAG CCG TTG TCC GAC ACC CAA TAC GGG TAC AAA                     1092
Lys Lys Val Leu Glu Pro Leu Ser Asp Thr Gln Tyr Gly Tyr Lys
                350                 355                 360

TCT CAA GTG AAC TAC GAT TTC TTT GCC CGT TTC CTG TGG TTC AAC                     1137
Ser Gln Val Asn Tyr Asp Phe Phe Ala Arg Phe Leu Trp Phe Asn
                365                 370                 375

TAC AAG CTC GAC TAT CTC GTT CAC AAG ACC GCC GGA ATC ATG CAA                     1182
Tyr Lys Leu Asp Tyr Leu Val His Lys Thr Ala Gly Ile Met Gln
                380                 385                 390

TTC CGA ACA ACT CTC GAG GAG AAG GCA AAG GCC AAG TAA                             1221
Phe Arg Thr Thr Leu Glu Glu Lys Ala Lys Ala Lys
                395                 400

AAGAATATCC CGTGCCGTTC TAGAGTACAA CAACAACTTC TGCGTTTTCA                          1271

CCGGTTTTGC TCTAATTGCA ATTTTTCTTT GTTCTATATA TATTTTTTTG                          1321

CTTTTTAATT TTATTCTCTC TAAAAAACTT CTACTTTCA GTGCGTTGAA                           1371

TGCATAAAGC CATAACTCTT                                                           1391
```

FIG. 1B

ω-3 FATTY ACID DESATURASE

CROSS REFERENCE TO RELATED CASE

This application claims the benefit of U.S. Provisional Application No. 60/038,409, filed Feb. 18, 1997, which is incorporated herein by reference.

ACKNOWLEDGMENT OF GOVERNMENT SUPPORT

This invention was made with Government support under Research Grant 95-37301-2287 from the USDA-NRICGP. The Government has certain rights to this invention.

BACKGROUND OF THE INVENTION

This invention relates to fatty acid metabolism, in particular to fatty acid desaturases.

Polyunsaturated fatty acids are important as structural components of membrane glycerolipids and as precursors of families of signaling molecules including prostaglandins, thromboxanes, and leukotrienes (Needleman et al., *Annu. Rev. Biochem.* 55:69–102, 1986; Smith and Borgeat, in *Biochemistry of Lipids and Membranes,* eds. Vance and Vance, Benjamin/Cummings, Menlo Park, Calif., 1986, pp. 325–360).

The principal fatty acid precursors of these signaling molecules are arachidonic acid ($\Delta 5,8,11, 14$–20:4), providing an ω-6 substrate that is responsible for the major synthesis of these compounds, and eicosapentanenoic acid ($\Delta 5,8,11,14,17$–20:5), an ω-3 substrate that is responsible for the parallel synthesis of many eicosanoids having an additional double bond. An important class of enzymes involved in the synthesis of polyunsaturated fatty acids is the fatty acid desaturases, which catalyze the introduction of double bonds into the hydrocarbon chain.

In vertebrates, desaturases are known to act at the $\Delta 4, 5, 6, 8$ and 9 positions (Holloway, In: *The Enzymes,* ed. Boyer, Academic Press, New York, vol. 16, 1983, pp. 63–83). The 18:0-CoA $\Delta 9$ desaturase from rat liver has been characterized biochemically (Strittmatter et al., *Proc. Natl. Acad. Sci. USA* 71:4565–4569, 1974; Thiede et al., *J. Biol. Chem.* 260:14459–14463, 1985), and the corresponding gene has been cloned (Thiede et al., *J. Biol. Chem.* 261:13230–13235, 1986). However, the remaining four enzymes have remained recalcitrant to purification and genes that encode them have not been isolated. Based on available information, and by analogy to the 18:0-CoA desaturase, it is likely that the remaining four enzymes are integral membrane proteins that require other membrane components (cytochrome $b_5$ and NADH:cytochrome $b_5$ reductase) for activity (Strittmatter et al., *Proc. Natl. Acad. Sci. USA* 71:4565–4569, 1974), and it is these features that have limited progress in studying the biochemistry and molecular genetics of these important synthetic reactions.

Biochemical studies of membrane-bound fatty acid desaturases in plants have proven equally difficult, and only one enzyme has been purified to homogeneity (Schmidt et al., *Plant Mol. Biol.* 26:631–642, 1994). Higher plants produce many different unsaturated fatty acids (Hilditch and Williams, *The Chemical Constituents of Natural Fats,* Chapman and Hall, London, 4th Ed., 1964), but in membrane lipids the major locations for double bonds are at the $\Delta 9, 12$ and 15 (ω-3) positions of 18-carbon acyl chains and the corresponding $\Delta 7, 10$ and 13 (ω-3) positions of 16-carbon chains (Browse and Somerville, *Ann. Rev. Plant Physiol. Plant Mol. Biol.* 42:467–5069, 1991).

SUMMARY OF THE INVENTION

According to one embodiment of the invention, a cell is provided that includes a recombinant FAT-1 polypeptide that desaturates an ω-6 fatty acid of the cell to a corresponding ω-3 fatty acid. FAT-1 is capable of desaturating ω-6 fatty acids having carbon chains of at least 18 carbons (e.g., 20- to 22-carbon fatty acids), and is significantly more efficient than FAD3, for example, at desaturating ω-6 fatty acids having carbon chains of 20 carbons or longer, producing lipids having at least 25% of 20-carbon ω-6 fatty acids desaturated to the corresponding ω-3 fatty acid. FAT-1 can desaturate double bonds at positions $\Delta 4, \Delta 5, \Delta 6, \Delta 7,$ and $\Delta 8$, for example. The expression of the FAT-1 polypeptide in a cell permits the cell to have a greater proportion of the ω-3 fatty acid than an otherwise similar cell lacking the FAT-1 polypeptide, including cells from a wide variety of organisms, such as bacteria, cyanobacteria, phytoplankton, algae, fungi, plants, and animals.

According to another aspect of the invention, the recombinant FAT-1 polypeptide has at least 60% amino acid sequence identity with the FAT-1 polypeptide shown in FIG. 1 (SEQ ID NO:1 and 2). In preferred embodiments, the recombinant FAT-1 polypeptide has only conservative amino acid substitutions to the FAT-1 polypeptide of FIG. 1.

According to another aspect of the invention, the recombinant FAT-1 polypeptide is encoded by a polynucleotide that includes a sequence having at least 70% nucleotide sequence identity with the fat-1 polynucleotide sequence of FIG. 1. For example, according to one embodiment, such a polynucleotide includes a full-length native fat-1 protein-coding region, e.g., the protein-coding region of the fat-1 polynucleotide sequence of FIG. 1.

According to another aspect of the invention, lipids are provided that are produced from such cells.

According to another aspect of the invention, transgenic plants are provided that include a fat-1 polynucleotide that is expressible in at least a part of the plant, e.g., in seeds of the plant. Also provided are seeds of such transgenic plants. Also provided are lipids from such transgenic plants that have higher proportions of ω-3 fatty acids than control lipids obtained from otherwise similar plants lacking the fat-1 polynucleotide.

According to another aspect of the invention, related methods of desaturating an ω-6 fatty acid to a corresponding ω-3 fatty acid are provided. Such methods comprise the steps of: (a) providing a cell that comprises a recombinant FAT-1 polypeptide; and (b) growing the cell under conditions under which the FAT-1 polypeptide desaturates an ω-6 fatty acid to produce a corresponding ω-3 fatty acid.

According to another aspect of the invention, related methods of producing a lipid comprising an ω-3 fatty acid are provided that include the steps of: (a) providing a lipid that includes an ω-6 fatty acid; and (b) desaturating at least some of the ω-6 fatty acid to a corresponding ω-3 fatty acid with a recombinant FAT-1 polypeptide. For example, such a method can be practiced by expressing a recombinant fat-1 nucleic acid in a cell, thereby producing a recombinant FAT-1 polypeptide in the cell.

The foregoing and other aspects of the invention will become more apparent from the following detailed description and accompanying drawings.

BRIEF DESCRIPTION OF THE DRAWINGS

FIG. 1 shows the nucleotide sequence of the fat-1 cDNA and the deduced amino-acid sequence of the FAT-1 polypeptide encoded by the cDNA.

DETAILED DESCRIPTION OF THE INVENTION

We have cloned fat-1, an ω-3 fatty acyl desaturase gene from *Caenorhabditis elegans*. When expressed in a wide range of host cells, the polypeptide encoded by fat-1 catalyzes the introduction of an ω-3 double bond into 18-, 20-, and 22-carbon fatty acids.

The *C. elegans* fat-1 gene encodes the first animal representative of a class of glycerolipid desaturases that have previously been characterized in plants and cyanobacteria. The FAT-1 protein is an ω-3 fatty acyl desaturase that recognizes a range of 18-, 20-, and 22-carbon ω-6 substrates. When expressed in a wide range of host cells, FAT-1 catalyzes the introduction of an ω-3 double bond into 18-, 20-, and 22-carbon fatty acids. The efficiency of FAT-1 in desaturating 20- and 22-carbon substrates appears to be much greater than FAD3 desaturase of Arabidopsis, for example.

A recombinant ω-3 fatty acyl desaturase polypeptide, e.g., a FAT-1 polypeptide, is useful for producing lipids having a higher proportion of ω-3 fatty acids, whether by means of recombinant expression in a cell or in an industrial processes using purified FAT-1 polypeptide. Such lipids are useful as food oils, as nutritional supplements, and as chemical feedstocks, for example.

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

Nucleic Acids

"Polynucleotide". A polynucleotide (or nucleic acid) sequence is a naturally-occurring or chemically-synthesized DNA or RNA sequence. A polynucleotide according to the invention may be single- or double-stranded.

"fat-1 Polynucleotide"; "fat-1 Gene". The terms "fat-1 polynucleotide" or "fat-1 gene" refer to a native FAT-1-encoding polynucleotide or a fragment thereof, e.g., a native *C. elegans* cDNA or genomic sequence or alleles, or fat-1 homologs from other species. The terms also encompass variant forms of a native fat-1 polynucleotide sequence or fragment thereof as discussed below, including polynucleotides that encodes a polypeptide having FAT-1 biological activity.

Native fat-1 sequences can include 5'- and 3'-flanking sequences or internal sequences operably linked to a native fat-1 polynucleotide sequence, including regulatory elements and/or intron sequences.

"FAT-1 Biological Activity". The term "FAT-1 biological activity" refers to a biological activity characteristic of a native FAT-1 polypeptide.

"Native". The term "native" refers to a naturally-occurring ("wild-type") polynucleotide or polypeptide.

"Homolog". A "homolog" of fat-1 is a polynucleotide from a species other than *C. elegans* that encodes a polypeptide that is functionally similar to FAT-1 and that preferably has at least 60% amino-acid sequence similarity, or more preferably, at least 60% sequence identity, to FAT-1.

"Isolated". An "isolated" polynucleotide is one that has been substantially separated or purified away from other polynucleotide sequences in the cell of the organism in which the polynucleotide naturally occurs, i.e., other chromosomal and extrachromosomal DNA and RNA, by conventional nucleic acid-purification methods. The term also embraces recombinant polynucleotides and chemically synthesized polynucleotides.

Fragments, Probes, and Primers. A fragment of a fat-1 polynucleotide is a portion of a fat-1 polynucleotide that is less than full-length and comprises at least a minimum length capable of hybridizing specifically with a native fat-1 polynucleotide under stringent hybridization conditions. The length of such a fragment is preferably at least 15 nucleotides, more preferably at least 20 nucleotides, and most preferably at least 30 nucleotides of a native fat-1 polynucleotide.

Polynucleotide probes and primers can be prepared based on a native fat-1 polynucleotide. A "probe" is an isolated polynucleotide to which is attached a conventional detectable label or reporter molecule, e.g., a radioactive isotope, ligand, chemiluminescent agent, or enzyme. A "primer" is an isolated polynucleotide that can be annealed to a complementary target DNA strand by nucleic acid hybridization to form a hybrid between the primer and the target polynucleotide strand, then extended along the target polynucleotide strand by a polymerase, e.g., a DNA polymerase. Primer pairs can be used for amplification of a polynucleotide sequence, e.g., by the polymerase chain reaction (PCR) or other conventional amplification methods.

Probes and primers are generally 15 nucleotides or more in length, preferably 20 nucleotides or more, more preferably 25 nucleotides, and most preferably 30 nucleotides or more. Such probes and primers hybridize specifically to a native *C. elegans* fat-1 polynucleotide under high stringency hybridization conditions and hybridize specifically to a native fat-1 sequence of another species under at least moderately stringent conditions. Preferably, probes and primers according to the present invention have complete sequence identity with the native *C. elegans* fat-1 sequence.

Methods for preparing and using probes and primers are described, for example, in *Molecular Cloning: A Laboratory Manual*, 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992); and Innis et al., *PCR Protocols: A Guide to Methods and Applications*, Academic Press: San Diego, 1990. PCR-primer pairs can be derived from a known sequence, for example, by using computer programs intended for that purpose such as Primer™ (Whitehead Institute for Biomedical Research, Cambridge, Mass.).

Primers and probes based on the native fat-1 sequence disclosed herein can be used to confirm (and, if necessary, to correct) the disclosed fat-1 nucleotide sequence by conventional methods, e.g., by re-cloning and sequencing a fat-1 cDNA or genomic sequence.

Nucleotide Sequence Identity. Nucleotide sequence "identity" or "similarity" is a measure of the degree to which two polynucleotide sequences have identical nucleotide bases at corresponding positions in their sequence when optimally aligned (with appropriate nucleotide insertions or deletions). Preferably, a fat-1 nucleotide sequence as defined herein has at least about 75% nucleotide sequence identity, preferably at least about 80% identity, more preferably at least about 85% identity, and most preferably at least about 90% identity with the *C. elegans* fat-1 cDNA sequence (SEQ ID NO:1). Such a degree of nucleotide sequence identity is considered "substantial" nucleotide sequence identity. Sequence identity can be determined by comparing the nucleotide sequences of two polynucleotides using sequence analysis software such as the Sequence Analysis Software Package of the Genetics Computer Group, University of Wisconsin Biotechnology Center, Madison, Wis.

Alternatively, two polynucleotides are substantially similar if they hybridize under stringent conditions, as defined below.

"Operably Linked". A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" polynucleotide is made by an artificial combination of two otherwise separated segments of sequence, e.g., by chemical synthesis or by the manipulation of isolated segments of polynucleotides by genetic engineering techniques.

Techniques for nucleic-acid manipulation are well-known (see, e.g., Sambrook et al., 1989, and Ausubel et al., 1992). Methods for chemical synthesis of polynucleotides are discussed, for example, in Beaucage and Carruthers, *Tetra. Letts.* 22:1859–1862, 1981, and Matteucci et al., *J. Am. Chem. Soc.* 103:3185, 1981. Chemical synthesis of polynucleotides can be performed, for example, using commercial automated oligonucleotide synthesizers.

Preparation of Recombinant or Chemically Synthesized Polynucleotides; Vectors, Transformation, Host cells. Natural or synthetic polynucleotides according to the present invention can be incorporated into recombinant nucleic-acid constructs, typically DNA constructs, capable of being introduced into, replicating in, and expressing a FAT-1 polypeptide in a host cell.

For the practice of the present invention, conventional compositions and methods for preparing and using vectors and host cells are employed, as discussed, inter alia, in Sambrook et al., 1989, or Ausubel et al., 1992.

A cell, tissue, organ, or organism into which has been introduced a foreign polynucleotide, such as a recombinant vector, is considered "transformed", "transfected", or "transgenic." A "transgenic" or "transformed" cell or organism also includes progeny of the cell or organism and progeny that carries the transgene, including, for example, progeny of sexual crosses between a transgenic parent and a non-transgenic parent that exhibit an altered phenotype resulting from the presence of a fat-1 polynucleotide construct.

Such a construct preferably is a vector that includes a replication system and sequences that are capable of transcription and translation of a polypeptide-encoding sequence in a given host cell. Expression vectors may include, for example, any well-known origin of replication or autonomously replicating sequence (ARS), expression control sequence, promoter, enhancer, secretion signal, ribosome-binding site, RNA splice site, polyadenylation site, transcriptional terminator sequence, mRNA stabilizing sequence, etc., that is operable in a given host. Such DNA constructs are prepared and introduced into a host cell(s) by conventional methods.

Expression and cloning vectors preferably also include a selectable or screenable marker appropriate for a given host cell or organism. Typical selection genes encode proteins that, for example (a) confer resistance to antibiotics or other toxic substances, e.g. ampicillin, neomycin, methotrexate, etc.; (b) complement auxotrophic deficiencies, or (c) supply critical nutrients not available from complex media.

The vectors containing the polynucleotides of interest can be introduced into a host cell by any well-known method, including electroporation; transfection employing calcium chloride, rubidium chloride calcium phosphate, DEAE-dextran, or other substances; microprojectile bombardment; lipofection; infection (where the vector is an infectious agent, such as T-DNA of Agrobacterium for plant cell transformation or a retroviral genome for animal cell transformation); etc.

The fat-1 gene is derived from *C. elegans* and, when expressed in plants and yeast, the gene product is biologically active. Therefore, it is expected that fat-1 can be successfully expressed and that the expressed FAT-1 polypeptide will be active in a wide variety of prokaryotic and eukaryotic hosts, including, but not limited to: bacteria, including Gram negative bacteria such as *Escherichia coli* and Gram-positive bacteria such as Bacillus (e.g., *B. subtilis*), cyanobacteria, phytoplankton, algae, fungi (including, but not limited to, yeast such as *Saccharomyces cerevisiae* and filamentous fungi), plants (including monocots and dicots), and animals (e.g., insect, avian, and mammalian species and marine organisms such as Schizochytrium spp.).

If a host cell does not naturally produce a substrate for FAT-1, one or more substrate molecules can be provided exogenously to cells transformed with an expressible fat-1 polynucleotide, or fat-1 can be co-expressed in cells together with one or more cloned genes that encode polypeptides that can produce substrate compounds from compounds available in such cells.

A recombinant fat-1 polynucleotide expression vector in a cell can be used to produce a recombinant FAT-1 polypeptide that is functional in the cell to desaturate an $\omega$-6 fatty acid, which is naturally produced by the cell or that is provided exogenously to the cell, to a corresponding $\omega$-3 fatty acid. In this way, a cell can be produced that has a higher proportion of $\omega$-3 fatty acids than an otherwise similar cell lacking the recombinant FAT-1 polypeptide. Alternatively, for example, an extracted lipid that includes an $\omega$-6 fatty acid can be treated with a FAT-1 polypeptide to desaturate an $\omega$-6 fatty acid to a corresponding $\omega$-3 fatty acid. Preferably at least 10% of an $\omega$-6 fatty acid is desaturated to the corresponding $\omega$-3 fatty acid, more preferably at least 20%, and most preferably at least 50%.

Nucleic-Acid Hybridization; "Stringent Conditions"; "Specific". The nucleic-acid probes and primers of the present invention hybridize under stringent conditions to a target DNA sequence, e.g., to a native fat-1 polynucleotide.

The term "stringent conditions" is functionally defined with regard to the hybridization of a nucleic-acid probe to a target polynucleotide (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968.

Regarding the amplification of a target nucleic-acid sequence (e.g., by PCR) using a particular amplification primer pair, "stringent conditions" are conditions that permit the primer pair to hybridize substantially only to the target nucleic-acid sequence to which a primer having the corresponding wild-type sequence (or its complement) would bind so as to produce a unique amplification product.

For hybridization of a probe or primer to a polynucleotide of another plant species in order to identify fat-1 homologs, preferred hybridization and washing conditions are as discussed in Sambrook et al., 1989 at 9.47–9.57, wherein "high stringency hybridization conditions" include hybridization at 65° C. in a hybridization solution that includes 6×SSC and washing for 1 hour at 65° C. in a wash solution that includes 0.5×SSC, 0.5% SDS. "Moderate stringency" conditions are similar except that the temperature for the hybridization and washing steps are performed at a lower temperature at which the probe is specific for a target sequence, preferably at least 42° C., more preferably at least 50° C., more preferably at 55° C., and most preferably at least 60° C.

The term "specific for (a target sequence)" indicates that a probe or primer hybridizes under given hybridization conditions substantially only to the target sequence in a sample comprising the target sequence. It is expected that hybridization of a *C. elegans* fat-1 probe or primer to genomic DNA or cDNA of another species will identify more than one hybridizing sequence in many cases, including fat-1 homologs and other sequences having substantial sequence identity with *C. elegans* fat-1, particularly other desaturase genes.

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications,* ed. Innis et al., Academic Press, San Diego, 1990.

Nucleotide- and Amino-Acid Sequence Variants. Using the fat-1 nucleotide and amino-acid sequences disclosed herein, those skilled in the art can create polynucleotides and polypeptides that have minor sequence variations from the corresponding native sequence.

"Variant" polynucleotides are polynucleotides containing minor changes in a native fat-1 polynucleotide sequence, i.e., changes in which one or more nucleotides of a native fat-1 polynucleotide is deleted, added, and/or substituted, preferably while substantially maintaining a biological activity of FAT-1. Variant polynucleotides can be produced, for example, by standard DNA mutagenesis techniques or by chemically synthesizing the variant polynucleotide molecule or a portion thereof. Such variants preferably do not change the reading frame of the protein-coding region of the polynucleotide and preferably encode a polypeptide having no change, only a minor reduction, or an increase in FAT-1 biological activity.

Amino-acid substitutions are preferably substitutions of single amino-acid residues. Insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant polynucleotides according to the present invention are "silent" or "conservative" variants. "Silent" variants are variants of a native fat-1 sequence or a homolog thereof in which there has been a substitution of one or more base pairs but no change in the amino-acid sequence of the polypeptide encoded by the polynucleotide. "Conservative" variants are variants of the native fat-1 polynucleotide or an allele or homolog thereof in which at least one codon in the protein-coding region of the polynucleotide has been changed, resulting in a conservative change in one or more amino-acid residues of the polypeptide encoded by the polynucleotide, i.e., an amino acid substitution. A number of conservative amino acid substitutions are listed below. In addition, one or more codons encoding cysteine residues can be substituted for, resulting in a loss of a cysteine residue and affecting disulfide linkages in the FAT-1 polypeptide.

TABLE 1

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Polypeptides

"FAT-1 Polypeptide". The term "FAT-1 polypeptide" (or protein) refers to a polypeptide encoded by a fat-1 polynucleotide, including alleles, homologs, and variants of a native fat-1 polynucleotide. A FAT-1 polypeptide can be produced by the expression of a recombinant fat-1 polynucleotide or can be chemically synthesized. Techniques for chemical synthesis of polypeptides are described, for example, in Merrifield, *J. Amer. Chem. Soc.* 85:2149–2156, 1963.

Polypeptide Sequence Identity and Similarity. FAT-1 polypeptides encompassed by the present invention have at least about 60% amino acid sequence similarity to the *C. elegans* FAT-1 polypeptide (SEQ ID NO:2), more preferably at least about 70% similarity, more preferably at least about 80% similarity, and most preferably at least about 95% similarity. Even more preferable are similar degrees of amino acid sequence identity. Such similarity (or identity) is considered to be "substantial" similarity (or identity), although more important than shared amino-acid sequence similarity can be the common possession of characteristic structural features and the retention of biological activity that is characteristic of FAT-1.

Amino acid sequence "identity" (or "homology") is a measure of the degree to which aligned amino acid sequences possess identical amino acids at corresponding positions. Amino acid sequence "similarity" is a measure of the degree to which aligned amino acid sequences possess identical amino acids or conservative amino acid substitutions at corresponding positions.

Amino acid sequence similarity and identity is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated," "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide that is chemically synthesized or recombinant (i.e., the product of the expression of a recombinant polynucleotide, even if expressed in a homologous cell type) is considered to be isolated. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high performance liquid chromatography; or other conventional methods.

It is expected that purified FAT-1 polypeptide will be useful for enzymatic conversion of ω-6 fatty acids to corresponding ω-3 fatty acids under conditions (e.g., detergent, salt, pH, temperature) suitable for FAT-1 enzymatic activity, for example, with FAT-1 polypeptide incorporated into liposomes or free in solution.

Protein Purification. The polypeptides of the present invention can be purified by any of the means known in the art. Various methods of protein purification are described, e.g., in *Guide to Protein Purification,* ed. Deutscher, *Meth. Enzymol.* 185, Academic Press, San Diego, 1990; and Scopes, *Protein Purification: Principles and Practice,* Springer Verlag, New York, 1982.

Variant and Modified Forms of FAT-1 Polypeptides. Encompassed by the FAT-1 polypeptides of the present invention are variant polypeptides in which there have been substitutions, deletions, insertions or other modifications of a native FAT-1 polypeptide. The variants substantially retain structural characteristics and biological activities of a corresponding native FAT-1 polypeptide and are preferably silent or conservative substitutions of one or a small number of contiguous amino acid residues.

A native FAT-1 polypeptide sequence can be modified by conventional methods, e.g., by acetylation, carboxylation, phosphorylation, glycosylation, ubiquitination, and labeling, whether accomplished by in vivo or in vitro enzymatic treatment of a FAT-1 polypeptide or by the synthesis of a FAT-1 polypeptide using modified amino acids.

Labeling. FAT-1 polypeptides can be labeled using conventional methods and reagents. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., 1989 and Ausubel et al., 1992.

Polypeptide Fragments. The present invention also encompasses fragments of a FAT-1 polypeptide that lacks at least one residue of a native full-length FAT-1 polypeptide. Preferably, such a fragment retains FAT-1 desaturase activity, possession of a characteristic functional domain, or an immunological determinant characteristic of a native FAT-1 polypeptide. Immunologically active fragments typically have a minimum size of 7 to 17 or more amino acids. Fragments retaining substantial desaturase activity are preferred, and can be obtained by deleting one or more amino acids from the N-terminus or the C-terminus of the polypeptide, for example.

Fusion Polypeptides. The present invention also provides fusion polypeptides including, for example, heterologous fusion polypeptides in which a FAT-1 polypeptide sequence is joined to a well-known fusion partner. Such fusion polypeptides can exhibit biological properties (such as substrate or ligand binding, enzymatic activity, antigenic determinants, etc.) derived from each of the fused sequences. Fusion polypeptides are preferably made by the expression of recombinant polynucleotides that include sequences for each of the fusion partners joined in frame.

Polypeptide Sequence Determination. The sequence of a polypeptide of the present invention is determined by any conventional method.

Antibodies

The present invention also encompasses polyclonal and/or monoclonal antibodies capable of specifically binding to a FAT-1 polypeptide and/or fragments thereof. Such antibodies are raised against a FAT-1 polypeptide or fragment thereof and are capable of distinguishing a FAT-1 polypeptide from other polypeptides, i.e., they are FAT-1-specific.

For the preparation and use of antibodies according to the present invention, including various immunoassay techniques and applications, see, e.g., Goding, *Monoclonal Antibodies: Principles and Practice,* 2d ed, Academic Press, New York, 1986; and Harlow and Lane, *Antibodies: A Laboratory Manual,* Cold Spring Harbor Laboratory, Cold Spring Harbor, N.Y., 1988. FAT-1-specific antibodies are useful, for example in: purifying a FAT-1 polypeptide from a biological sample, such as a host cell expressing a recombinant FAT-1 polypeptide; in cloning a fat-1 allele or homolog from an expression library; as antibody probes for protein blots and immunoassays; etc.

Such antibodies can be labeled by any of a variety of conventional methods. Suitable labels include, but are not limited to, radionuclides, enzymes, substrates, cofactors, inhibitors, fluorescent agents, chemiluminescent agents, magnetic particles, etc.

Obtaining Alleles and Homologs of fat-1

Based upon the availability of the fat-1 cDNA sequence disclosed herein, genomic clones and alleles and homologs of the disclosed fat-1 sequence can be obtained by conventional methods, e.g., by screening a cDNA or genomic library with a probe that specifically hybridizes to a native fat-1 polynucleotide under at least moderately stringent conditions, by PCR or another amplification method using a primer or primers that specifically hybridize to a native fat-1 polynucleotide under at least moderately stringent conditions, or by identification of fat-1 alleles or homologs in an expression library using FAT-1-specific antibodies. The identity of fat-1 alleles or homologs can be confirmed by application of an exogenous ω-6 fatty acid substrate to cells (e.g., bacterial, yeast, or plant cells) in which the cloned fat-1 gene is expressed, followed by gas chromatography analysis to determine whether the cloned gene converts the ω-6 substrate to the corresponding ω-3 fatty acid, for example.

Probes and primers based on the fat-1 sequence disclosed herein can also be used to obtain closely related genes having substantial nucleotide sequence identity to fat-1, e.g., other desaturase genes, including other ω-3 fatty acyl desaturase genes, by conventional methods.

Plant Transformation and Regeneration

Nucleic-acid constructs that include a fat-1 polynucleotide are useful for producing transgenic plants that are capable of efficiently converting ω-6 fatty acids, including fatty acids having a carbon chain of greater than 18 carbons (e.g., 20, 22, or 24 carbons), to the corresponding ω-3 fatty acids, thus producing plant cells and lipids obtained therefrom that have an altered fatty acid profile. Such plants include plants that are commonly grown for oil production, including, but not limited to, rapeseed, corn, canola, safflower, soybean, sunflower, peanut, etc.

A number of vectors suitable for stable transfection of plant cells or for the establishment of transgenic plants have been described in, e.g., Pouwels et al., *Cloning Vectors: A Laboratory Manual*, 1985, supp. 1987); Weissbach and Weissbach, *Methods for Plant Molecular Biology*, Academic Press, 1989; and Gelvin et al., *Plant Molecular Biology Manual*, Kluwer Academic Publishers, 1990.

Examples of constitutive plant promoters useful for expressing fat-1 polynucleotides include but are not limited to: the cauliflower mosaic virus (CaMV) 35S promoter, which confers constitutive, high-level expression in most plant tissues (see, e.g., Odel et al., *Nature* 313:810, 1985), including monocots (see, e.g., Dekeyser et al., *Plant Cell* 2:591, 1990; Terada and Shimamoto, *Mol. Gen. Genet.* 220:389, 1990); the nopaline synthase promoter (An et al., *Plant Physiol.* 88:547, 1988) and the octopine synthase promoter (Fromm et al., *Plant Cell* 1:977, 1989).

A variety of plant gene promoters that are regulated in response to environmental, hormonal, chemical, and/or developmental signals, also can be used for expression of a fat-1 polynucleotide in plant cells. Seed-specific promoters are preferred, but such regulated promoters may also include promoters regulated by: (1) heat (Callis et al., *Plant Physiol.* 88:965, 1988); (2) light (e.g., pea rbcS-3A promoter, Kuhlemeier et al., *Plant Cell* 1:471, 1989; maize rbcS promoter, Schaffner and Sheen, *Plant Cell* 3:997, 1991; or chlorophyll a/b-binding protein promoter, Simpson et al., *EMBO J.* 4:2723, 1985); (3) hormones, such as abscisic acid (Marcotte et al., *Plant Cell* 1:969, 1989); (4) wounding (e.g., wunI, Siebertz et al., *Plant Cell* 1:961, 1989); or (5) chemicals such as methyl jasmonate, salicylic acid, or safeners.

In addition, vectors for plant expression can include additional regulatory sequences from the 3'-untranslated region of plant genes (Thornburg et al., *Proc. Natl. Acad. Sci. USA* 84:744 (1987); An et al., *Plant Cell* 1:115 (1989), e.g., a 3' terminator region to increase mRNA stability of the mRNA, such as the PI-II terminator region of potato or the octopine or nopaline synthase 3' terminator regions.

Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase).

Any well-known method can be employed for plant cell transformation, culture, and regeneration in the practice of the present invention with regard to a particular plant species. Conventional methods for introduction of foreign DNA into plant cells include, but are not limited to: (1) Agrobacterium-mediated transformation (Lichtenstein and Fuller, in: *Genetic Engineering,* Vol 6, Rigby, ed., London, Academic Press, 1987; and Lichtenstein and Draper, in: *DNA Cloning,* Vol II, Glover, ed., Oxford, IRl Press, 1985); (2) particle delivery (see, e.g., Gordon-Kamm et al., *Plant Cell* 2:603, 1990; or BioRad Technical Bulletin 1687); (3) microinjection (see, e.g., Green et al., *Plant Tissue and Cell Culture,* Academic Press, New York, 1987); (4) polyethylene glycol (PEG) procedures (see, e.g., Draper et al., *Plant Cell Physiol.* 23:451, 1982); Zhang and Wu, *Theor. Appl. Genet.* 76:835, 1988); (5) liposome-mediated DNA uptake (see, e.g., Freeman et al., *Plant Cell Physiol.* 25:1353, 1984); (6) electroporation (see, e.g., Fromm et al., *Nature* 319:791, 1986); and (7) vortexing methods (see, e.g., Kindle, *Proc. Natl. Acad. Sci. USA* 87:1228, 1990).

The term "plant" encompasses any higher plant and progeny thereof, including monocots (e.g., lily, corn, rice, wheat, barley, etc.), dicots (e.g., tomato, potato, soybean, cotton, tobacco, etc.), and includes parts of plants, including reproductive units of a plant (e.g., seeds, fruit, flowers, etc.)

A "reproductive unit" of a plant is any totipotent part or tissue of the plant from which one can obtain a progeny of the plant, including, for example, seeds, cuttings, tubers, buds, bulbs, somatic embryos, cultured cells (e.g., callus or suspension cultures), etc.

Transformation of Algal Cells

Nucleic-acid constructs that include a fat-1 polynucleotide are also useful for recombinant expression in algal cells, including plankton, that are capable of efficiently converting ω-6 fatty acids to the corresponding ω-3 fatty acids. Manipulation of algal cells in general is discussed, for example, in Dunahay et al., *Appl. Biochem. Biotechnol.* 57/58:223–231, 1996 and Dunahay et al., *J. Phycol.* 31:1004–1012, 1995.

The invention will be better understood by reference to the following Examples, which are intended to merely illustrate the best mode now known for practicing the invention. The scope of the invention is not to be considered limited thereto.

EXAMPLES

Example 1

The Cloning and Sequencing of a cDNA Encoding fat-1, an Animal Omega-3 Desaturase In Arabidopsis there are seven membrane desaturases. The biochemistry and function of these membrane desaturases has been facilitated by the availability of mutants with altered fatty acid compositions (Browse et al., *Science* 227:763–765, 1985) (Browse and Somerville, In: *Arabidopsis,* Cold Spring Harbor Press, New York, 1994, pp. 881–912). Genes encoding desaturases in Arabidopsis have been cloned (Arondel et al., *Science* 258:1353–1355, 1992; Yadav et al., *Plant Physiol.* 103:467–476, 1993; Yadav et al. in: *Biochemistry and Molecular Biology of Membrane and Storage Lipids of Plants,* ed. Murala and Somerville, American Society of Plant Physiologists, 1993, pp. 60–66; Okuley et al., *Plant Cell* 6:147–158, 1994). All the plant membrane-bound desaturases use complex glycerolipids rather than acyl-CoAs as substrates. This finding, together with data indicating that the Δ5 desaturase from rat liver acts on glycerolipids (Pugh and Kates, *J. Biol. Chem.* 252:68–73, 1977), suggested the possibility that the majority of animal desaturases also catalyze glycerolipid-linked desaturation. However, there has been little progress in characterizing other animal desaturases. In animals, fatty acid desaturases catalyze key reactions in the synthesis of arachidonic acid and other polyunsaturated fatty acids.

C. elegans elaborates a wide range of polyunsaturated fatty acids, including arachidonic (20:4, ω-6) and eicosapentaenoic acids (20:5, ω3) from very simple precursors available in the diet of the organism (Hutzell and Krusberg, Comp. Biochem. Physiol. 73B:517–520, 1982; Satouchi et al., Lipids 28:837–840, 1993). The ω-3 fatty acids (Δ9,12, 15–18:3; Δ8,11,14, 17–20:4 and Δ5,8,11,14,17–20:5) account for 17% of the total fatty acids in C. elegans (Hutzell and Krusberg, Comp. Biochem. Physiol. 73B:517–520, 1982) and 20:5 ω-3 is the major fatty acid in phosphatidylcholine from this organism (Satouchi et al., Lipids 28:837–840, 1993). These lipids are produced even when the worms are grown exclusively on E. coli, which provides only saturated and monounsaturated fatty acids (Satouchi et al., Lipids 28:837–840, 1993). Evidently, C. elegans must contain all the enzymes required for the synthesis of these highly unsaturated acyl groups.

We searched the National Center for Biotechnology Information's (NCBI) peptide sequence data base using a BLAST server with the peptide sequences of the Arabidopsis thaliana FAD2, FAD6 and FAD7 fatty acid desaturases as queries. (The GenBank accession numbers for the corresponding Arabidopsis cDNAs are L26296, U09503 and L22931, respectively.) The highest scoring C. elegans expressed sequence tag (EST) clones were NCBI-5443, NCBI-5881 and NCBI-5049. (The corresponding GenBank accession numbers were Z14935, M88884 and Z14543, respectively.) An alignment of cDNA sequences revealed a common identity of 301 bp among all three clones, indicating that the three ESTs originated from a single gene. The greatest amount of sequence data (486 bp) was available from EST clone NCBI-5881. This clone was requested from its origin at the C. elegans genome Sequencing Center, Washington University School of Medicine, St. Louis, Mo., with its original source identifier (CEL10ell). Upon receipt of CEL10ell, its identity was confirmed by partial sequencing.

In order to obtain a full-length cDNA corresponding to CEL10ell, the cDNA insert was released by double digestion with HindIII and SacI, gel purified, and labeled with $^{32}$P-dCTP using a random priming kit (Promega, Madison, Wis.). The denatured probe was used to screen a mixed stage C. elegans cDNA lambda phage (Uni-Zap XR) library (Stratagene, La Jolla, Calif.). Nucleic acid hybridizations and high stringency washes were performed as described (Amasino, Anal. Biochem. 152:304–307, 1986). Thirteen hybridizing plaques were visualized by autoradiography. The longest eight clones were all approximately 1.4 kb in length as judged by agarose gel electrophoresis. Positive clones were isolated and excised from the phage vector according to the manufacturer's protocol to yield pBluescript™ plasmids.

The plasmid clone with the longest insert, pCE8, was fully sequenced in both directions and found to contain a 1,410 bp cDNA insert. Sequence analysis was carried out using the programs available in the GCG package (Devereaux et al., Nucl. Acids Res. 12:387–395, 1984) using default settings for parameters unless otherwise indicated. This sequence was deposited in GenBank under Accession Number L41807.

The nucleotide sequence of the fat-1 cDNA (1391 nt) and the deduced FAT-1 amino-acid sequence are shown in FIG. 1 (and SEQ ID NO:1 and 2).

The DNA sequence corresponding to the open reading frame of the fat-1 cDNA was used to search the database of the C. elegans genome sequencing project using the BLAST server (Waterston and Sulston, Proc. Natl. Acad. Sci. USA 92:10836–10840, 1995). No homologous sequence was found (highest BLAST score: 145; p=0.034), indicating that the fat-1 genomic sequence had not yet been included in this project.

The cDNA insert in pCE8 contained an open reading frame that would be expected to encode a protein of 402 amino acids, with a molecular mass of 46.4 kD. Sequence comparisons were made using the programs of the Genetics Computer Group Package (Devereaux et al., Nucl. Acids Res. 12:387–395, 1984). The predicted amino acid sequence of the protein showed several regions of common homology with the predicted sequences of the FAD2 and FAD3 desaturases of Arabidopsis. Alignment with FAD2 revealed 35% sequence identity and 61% similarity (i.e., including both identical amino acid residues and conservative substitutions). Alignment with FAD3 indicated 32% sequence identity and 54% similarity. The FAD2 and FAD3 genes are known to encode enzymes that desaturate oleate (FAD2) or linoleate (FAD3) esterified to phosphatidylcholine of the endoplasmic reticulum (Arondel et al., Science 258:1353–1355, 1992; Okuley et al., Plant Cell 6:147–158, 1994). Within a tripartite alignment of the three sequences are 69 residues common to all three sequences, including eight histidines (amino acids 123, 127, 159, 162 163, 324, 327 and 328 in the C. elegans sequence) whose presence and locations are highly conserved among all the membrane desaturases (Okuley et al., Plant Cell 6:147–158, 1994). These findings strongly indicate that the gene represented by the pCE8 cDNA encodes a fatty acid desaturase or a related enzyme function. We have designated this gene fat-1 (Fatty Acid Metabolism-1).

It is somewhat surprising that the C. elegans gene shows a similar amino acid sequence homology to each of the two Arabidopsis desaturases, especially in view of the fact that the FAD2 and FAD3 sequences are relatively divergent, with only 37% common amino acid identity (Okuley et al., Plant Cell 6:147–158, 1994). From these comparisons alone, it is difficult to deduce whether the fat-1 gene is likely to represent a Δ12 desaturase (like FAD2), an ω-3 desaturase (like FAD3), or a more distantly related enzyme.

In contrast with the identity found between the deduced FAT 1 polypeptide sequence and FAD2 and FAD3 of Arabidopsis, there was only 17–23% homology to the yeast and rat genes that encode 18:0-CoA desaturases, only slightly above the level from comparisons with entirely unrelated genes. For this reason, it is unlikely that a database search using an 18:0-CoA desaturase as the query could have identified the fat-1 sequence.

The predicated protein sequence of the fat-1 gene product includes the three histidine-rich sequences that are highly conserved among all the membrane-bound fatty acid desaturases and that are believed to be the residues that coordinate the diiron-oxo structure at the active site of these enzymes (Shanklin et al., Biochemistry 33:12787–12794, 1994; Stukey et al., J. Biol. Chem. 265:20144–20149, 1990). Furthermore, two long stretches (>40 residues each) of hydrophobic residues are present (80 to 124 and 229 to 284). The length of these stretches and their positions relative to the conserved histidine sequences are similar to other desaturases. Therefore, the FAT-1 protein could conform with the model proposed by Stukey et al. (Stukey et al., J. Biol. Chem. 265:20144–20149, 1990), in which the bulk of the protein is exposed on the cytosolic face of the endoplasmic reticulum, while two membrane-traversing loops (each comprised of two membrane-spanning α-helical segments)

lock the protein into the bilayer. In common with many, though not all, of the proposed endoplasmic reticulum desaturases, the FAT-1 protein contains a carboxy-terminal motif (KAKAK) that conforms to a consensus retention signal for transmembrane proteins in the endoplasmic reticulum (Jackson et al., *EMBO J.* 9:3153–3162, 1990).

These features are consistent with FAT-1 being a member of the membrane-bound desaturase/hydroxylase family of diiron-oxo proteins (Shanklin et al., *Biochemistry* 33:12787–12794, 1994). However, the FAT-1 sequence shows equal homology to both the Δ12 glycerolipid desaturase encoded by FAD2 and the ω-3 glycerolipid desaturase encoded by FAD3.

Example 2

Expression of fat-1 in Arabidopsis and Characterization of its Function

To determine which class of reaction is catalyzed by FAT-1 and to explore the substrate chainlength and regiochemical specificities of the enzyme it was necessary to use heterologous expression of a fat-1 cDNA in a host that contained potential fatty acid substrates. Both *Escherichia coli* and *Saccharomyces cerevisiae*, which are two common laboratory hosts for heterologous expression, possess a very limited range of endogenous desaturation activities and hence fatty acid compositions. By contrast, plants possess both a wider range of desaturase activities and fatty acids that are potential substrates for a desaturase of unknown function. In addition, the lipid and fatty acid metabolism of plants, especially Arabidopsis, have been well characterized. These features make Arabidopsis a more attractive host for transgenic studies of putative eukaryotic fatty acid desaturases than either *E. coli* or *S. cerevisiae*.

In higher plants, desaturases have been characterized from two cellular compartments. Enzymes localized to the chloroplast (or plastid) use soluble ferredoxin as the electron donor for the reaction (Schmidt et al., *Plant Mol. Biol.* 26:631–642, 1994; Heinz, in *Lipid Metabolism in Plants,* ed., CRC Press, Boca Raton, Fla., 1993, pp. 33–89). Enzymes localized to the endoplasmic reticulum (including the FAD2 and FAD3 gene products) are similar to known yeast and animal desaturases inasmuch as they rely on cytochrome $b_5$ and cytochrome $b_5$ reductase to supply electrons from NAD(P)H (Heinz, in *Lipid Metabolism in Plants,* ed., CRC Press, Boca Raton, Fla., 1993, pp. 33–89). Mutants deficient in each of the major desaturases are available in Arabidopsis (Browse and Somerville, in *Arabidopsis,* ed. Cold Spring Harbor Press, New York, pp. 881–912, 1994). Genes that encode the 18:0-CoA desaturases from yeast and mammals have been expressed in plants and shown to alter the fatty acid compositions of the plant tissues (Polashok et al., *Plant Physiol.* 100:894–901, 1992; Grayburn et al., *Bio/Technology* 10:675–677, 1992). These considerations indicated that Arabidopsis is a suitable heterologous system to study the expression and function of the fat-1 gene.

In order to produce a fat-1 gene construct for plant expression, the cauliflower mosaic virus (CaMV) 35S promoter/nopaline synthase terminator cassette of Baulcombe et al. (Baulcombe et al., *Nature* 321:446–449, 1986) was cloned into the XbaI/EcoRI sites of pBIN400 (Spychalla and Bevan, In: *Plant Tissue Culture Manual: Fundamentals and Applications,* ed. Lindsay, Kluwer Academic Publishers, Dordrecht, Vol. B11, 1993 pp. 1-18) to make the binary transformation vector pBIN420. The cDNA insert of pCE8 was released with a EcoRI/KpnI double digest, end-filled with Klenow fragment, and blunt-ligated into the SmaI site of pBIN420 to make pBIN420-CE8. These vectors contain the NPTII gene within their T-DNA, thus conferring kanamycin resistance to transgenic plants.

The Columbia ecotype of the wild-type line of *Arabidopsis thaliana* (L.) Heynh. was used for plant transformation. The binary vector pBIN420-CE8 was introduced into the Agrobacterium strain PC2760 by the freeze-thaw method (Holsters et al., *Mol. Gen. Genet.* 163:181–187, 1978). Agrobacterium-mediated transformation was accomplished with the in planta vacuum-infiltration method (Bouchez et al., *C. R. Acad. Sci. Paris* 316:1188–1193, 1993). Primary generation transformed seeds were selected on plates containing Murashige and Skoog basal salts (4.3 g/L), 1% (w/v) sucrose, 0.8% (w/v) Bacto-Agar, 200 mg/L carbenicillin, and 50 mg/L kanamycin, and was adjusted to pH 5.8 with KOH. In vitro roots were grown from sterilized seeds placed on vertical plates at 23° C. under continuous illumination (50–100 micromol quanta $m^{-2}s^{-1}$). The media for in vitro roots contained Gamborg B5 salts (3.1 g/L), 2% (w/v) glucose, and 0.2% Phytagel™ (Sigma, St. Louis, Mo.), and was adjusted to pH 5.8 with KOH.

Five individual transformants were obtained and allowed to set seed. Lines #9.7 and #10.5 were selected for further analysis by Southern and Northern blotting using the HindIII/SacI fragment of pCE8 as a probe on the RNA and DNA blots. Probe labeling, hybridizations and washings were as described above for cDNA library screens.

For Southern blots, genomic DNA was isolated from lines #9.7 and #10.5 according to the method of Dellaporta et al. (Dellaporta et al., *Plant Mol. Biol. Rep.* 1:19–21, 1983), restricted with BamHI, separated by agarose gel-electrophoresis, and alkaline blotted to nylon membranes. The Southern blot confirmed the presence of at least one copy of the transgene in line #9.7 and at least two copies in line #10.5.

For Northern blots, total RNA was extracted from leaves according to the method of Verwoerd et al. (Verwoerd et al., *Nucl. Acids Res.* 17:2362, 1989). Twenty-five micrograms of total RNA was separated on 1.2% agarose-formaldehyde gels and blot transferred to nylon membranes. Northern blots of total RNA from plants of the two lines and wild-type Arabidopsis showed that the appropriate fat-1 transcript accumulated in both transgenic lines. Plants from line #9.7 consistently produced higher transcript levels than line #10.5.

Characterization of Arabidopsis lipid mutants has indicated that lesions in the fad2 and fad3 genes are partly masked in leaf tissue by action of the chloroplast desaturases (encoded by FAD6, FAD7 and FAD8). For this reason, a first attempt to determine the function of the fat-1 gene product was made by analyzing the overall fatty-acid composition of root tissues from wild-type and fat-1 transgenic plants. The data in Table 2 show very large increases in the proportion of 18:3 in both transgenic lines compared with wild-type Arabidopsis. These increases were accompanied by concomitant decreases in the proportion of 18:2 but no significant changes in the levels of any other fatty acid. The alterations in root fatty-acid composition induced by expression of the *C. elegans* fat-1 gene are comparable to those observed by overexpression of the plant FAD3 gene (Arondel et al., *Science* 258:1353–1355, 1992). The FAT1 protein is thus operating as an efficient ω-3 desaturase in Arabidopsis.

TABLE 2

Composition (mol %) of total fatty acids from in vitro grown roots of the wild type (WT) and two transgenic lines (#9.7 and #10.5) of Arabidopsis expressing a *C. elegans* fat-1 cDNA[1]

| Genotype | 16:0  | 16:1(c) | 18:0 | 18:1  | 18:2  | 18:3  |
|----------|-------|---------|------|-------|-------|-------|
| WT       | 16.8a | 1.2a    | 1.4a | 22.7a | 39.3a | 18.0b |
| #9.7     | 17.8a | 1.2a    | 2.2a | 21.7a | 22.7b | 33.7a |
| #10.5    | 17.5a | 1.0a    | 1.6a | 20.9a | 23.7b | 34.5a |

[1] Values are means of quadruplicate measurements. Values for each fatty acid with the same letter do not differ significantly (p < 0.01).

In untreated Arabidopsis, linolenic acid (Δ9,12,15–18:3) is the only significant product resulting from fat-1 expression. However, *C. elegans* contains a wider range of PUFAs than does Arabidopsis. Three ω-3 fatty acids are present in the membrane lipids of the worm, of which linolenic acid is the least abundant (0.15% of total fatty acids). The 20-carbon fatty acids Δ8,11,14,17-eicosatetraenoic acid (an isomer of arachidonic acid) and Δ5,8,11,14,17-eicosapentaenoic acid (the expected product of ω-3 desaturation of arachidonic acid) account for 7.7% and 8.7% of total fatty acids, respectively (Hutzell and Krusberg, *Comp. Biochem. Physiol.* 73B:517–520, 1982).

Exogenous fatty acids applied to Arabidopsis leaves as sodium soaps are readily taken up and incorporated into membrane glycerolipids to levels that correspond to 2–5% of the total leaf lipids (McConn and Browse, *Plant Cell* 8:403–416, 1996). To test whether the fat-1-encoded desaturase is likely to be involved in synthesis of the 20-carbon ω-3 fatty acids in *C. elegans*, wild-type and transgenic Arabidopsis plants were sprayed once a day for twenty days with solutions of the sodium salts of arachidonic acid (Δ5,8,11,14–20:4) or a homogamma linolenic acid (Δ8,11,14–20:3).

For exogenous fatty-acid treatments, plants were grown in a growth chamber at 20° C. on a 12 h day/night cycle. Fatty-acid treatments began when the plant rosettes reached approximately 2 cm in diameter. Sodium soaps of homogamma-linolenic acid (Δ8,11,14–20:3) and arachidonic acid (Δ5,8,11,14–20:4) (NuCheck Prep, Elysian, Minn.) were made to a 0.1% aqueous solution and frozen in 5 mL aliquots. Plants were sprayed daily at the beginning of the dark period using a perfume atomizer. Groups of fifteen plants were sprayed with 5 mL of soap solution for 20 consecutive days.

Methods for extraction and separation of lipids, and for the preparation of fatty acid methyl esters have been described previously (Miquel and Browse, *J. Biol. Chem.* 267:1502–1509, 1992). Analysis of fatty acid methyl esters by gas chromatography was carried out using a 15 m×0.53 mm Supelcowax column (Supelco, Bellefonte, Pa.) with flame ionization detection. The initial column temperature of 160° C. was held for 1 min, then raised at 20° C./min to 190° C., followed by a ramp of 5° C./min to 230° C. The final temperature was held for 5 min. When wild-type and fat-1 transgenic plants were sprayed with exogenous fatty acids, the peaks for the ω-6 substrates, Δ8,11,14–20:3, Δ5,8,11,14–20:4 and of the ω-3 desaturation products Δ8,11,14,17–20:4 and Δ5,8,11,14,17–20:5 were identified based on their coelution with authentic standards (NuCheck Prep, Elysian, Minn.) and on the results of gas chromatography-mass spectrometry (GC-MS) analysis. For this analysis, fatty acid methyl esters derived from phosphatidylcholine were separated on a 30 m×0.2 mm AT1000 column (Alltech Assoc., Deerfield, Ill.) in a HP6890 Instrument (Hewlett-Packard, Avondale, Pa.). Oven temperature at injection was 50° C. and this was increased at 5° C./min to 230° C., then held at 230° C. for 10 min. Criterion for identification of Δ5,8,11,14,17–20:5 in phosphatidylcholine from fat1 transgenic plants were: (1) the identification of a mass peak at m/z=316, which corresponds to the expected molecular ion, and (2) a retention time (36.11 min) and fragmentation pattern identical to those of the authentic Δ5,8,11,14, 17–20:5 standard. No commercial standard was available for Δ8,11,14,17–20:4. A fatty acid methyl ester present in fat-1 transgenic plants sprayed with Δ8,11,14–20:3, but not in wild-type control plants, had a retention time of 35.74 min during GC-MS. This compound showed a mass peak at m/z=318 (the expected molecular ion for 20:4) and a fragmentation pattern very similar to that of the authentic Δ5,8,11,14–20:4 standard. The retention time of Δ5,8,11, 14–20:4 was 35.04 min for both the authentic standard and for the methyl esters recovered from plants sprayed with soaps of this isomer. Therefore, it was concluded that the new compound detected only in fat-1 transgenic plants sprayed with Δ8,11,14–20:3 was an isomer of 20:4 and most probably Δ8,11,14,17–20:4.

Analyses of total leaf lipids indicated that the exogenously supplied fatty acids were incorporated at levels of 1–3% of the total fatty acids. There was extensive incorporation into phosphatidylcholine, which is the major lipid of the endoplasmic reticulum and the major substrate for the plant 18:1 and 18:2 desaturases (Miquel and Browse, *J. Biol. Chem.* 267:1502–1509, 1992; Browse et al., *J. Biol. Chem.* 268:16345–16351, 1993). In wild-type leaves, the peak corresponding to Δ5,8,11,14–20:4 or Δ8,11,14–20:3 accounted for approximately 3–5% of the total fatty acids in phosphatidylcholine, but there was no detectable conversion of either of these fatty acids to their ω-3 unsaturated derivatives. By contrast, in leaves from plants expressing the fat-1 cDNA, the peaks corresponding to the exogenously-supplied ω-6 fatty acids were substantially replaced by peaks that correspond to the expected ω-3 desaturated products, Δ5,8,11,14,17–20:5 and Δ8,11,14,17–20:4. Thus, in contrast to the Arabidopsis FAD3 gene product, the *C. elegans* FAT-1 protein is a desaturase that acts on a range of ω-6 fatty acid substrates. These results demonstrate that the fat-1 gene encodes an ω-3 desaturase that is able to carry out the final step in the synthesis of all these fatty acids.

Example 3
Relative Efficiencies of the FAT-1 and FAD-3 Desaturases

A fat-1 cDNA confers to Arabidopsis plants the ability to desaturate 20:3, ω-6 and 20:4, ω-6 fatty acyl groups to the corresponding ω-3 products (Δ8,11,14,17–20:4 and Δ5,8,11, 14,17–20:5, respectively). The absence of detectable levels of these ω-3 fatty acids from untransformed Arabidopsis tissues suggests that the endogenous plant ω-3 desaturases (the FAD3, FAD7 and FAD8 enzymes in Arabidopsis) have little or no ability to desaturate 20-carbon substrates. However, the fat-1 cDNA is highly expressed in the transgenic plant line #9.7.

To more accurately compare the relative efficiencies of the FAT-1 and FAD3 desaturases, we used a transgenic Arabidopsis line (wild-type:pTiDES3) in which the FAD3 gene is overexpressed to a high degree (Arondel et al., *Science* 258:1353–1355, 1992). Proportions of 18:2 and 18:3 in the root fatty acid composition produced in this line are altered to a slightly greater degree than in line #9.7, indicating that the FAD3-overexpressing line contains a somewhat higher activity for ω-3 desaturation of 18:2 fatty acyl groups. However, when plants of the wild-type:pTiDES3 line were supplied with exogenous 20:4, ω-6 fatty acids using the protocol described above, less than 25% of this compound was converted to 20:5, ω-3 as judged by fatty acid analysis of phosphatidylcholine purified from leaf tissue of the sprayed plants. The low extent of conversion confirms that the enzyme encoded by the fat-1 cDNA is considerably more efficient than the plant FAD3 enzyme when 20:4, ω-6, is the substrate for ω-3 desaturation.

The ability of Arabidopsis plants to take up exogenous fatty acids provided us with a means to extend the biochemical characterization of the FAT-1 desaturase by showing that all the 18- and 20-carbon ω-6 fatty acids normally present in C. elegans are recognized as its substrates, as well as 22:5, ω-6 (i.e., Δ4,7,10,13,16–22:5). The FAD2 and FAD3 desaturases are known to use membrane glycerolipids, not acyl-CoAs, as substrates (Miquel and Browse, J. Biol. Chem. 267:1502–1509, 1992; Browse et al., J. Biol. Chem. 268:16345–16351, 1993). The high efficiency with which the FAT-1 enzyme desaturates the 18:2 of Arabidopsis membrane lipids and the high homology of FAT-1 to FAD2 and FAD3 strongly suggest that FAT-1 is also a glycerolipid desaturase. In this respect the enzyme is similar to the Δ5 desaturase activity described in rat liver (Pugh and Kates, J. Biol. Chem. 252:68–73, 1977). Other desaturases required for the synthesis of arachidonic acid in mammals may also use membrane phospholipids as their substrates.

Example 4 fat-1 Transgenic Arabidopsis Plants Desaturate Δ4,7,10,13, 16–22:5 to Δ4,7,10,13,16,19–22:6

The 22-carbon fatty acids docosapentaenoic acid (22:5, ω-6) and docosahexaenoic acid (22:6, ω-3) also have important dietary and pharmaceutical uses. For many applications, 22:6, ω-3 is the more desirable product. Most sources of 22-carbon highly unsaturated fatty acids contain both 22:5, ω-6 and 22:6, ω-3. We therefore investigated whether FAT-1 could desaturate 22:5, ω-6 to the ω-3 product.

For this purpose, plants of the transgenic Arabidopsis line #9.7, which express FAT-1, were grown together with control wild-type plants at 24° C. with continuous illumination under fluorescent lights (150 μmol quanta/m²/s). Sets of 15 leaves from 20-day-old wild-type or fat-1 transgenic plants were harvested and placed in 2-inch diameter petri dishes. To each petri dish was added either 4 mL of an aqueous solution containing 1% (v/v) dimethylsulfoxide and 0.025% (wt/v) of the potassium soap of 22:5 ω-6 fatty acid or 4 mL of a similar solution lacking the 22:5 ω-6 soap. Each dish was covered with a single layer of absorbent tissue to ensure good contact between the solution and the leaves, closed, covered with aluminum foil, and incubated in the dark for four hours. After the solution was removed, the leaves were rinsed several times with distilled water, then covered with 4 mL of water and incubated under fluorescent lights (150 μmol quanta/m²/s) for an additional 24 hours before lipid extraction.

Methods for extraction and separation of lipid classes and for the preparation of fatty acid methyl esters have been described previously (Miquel and Browse, J. Biol. Chem. 267:1502–1509, 1992). Analysis of fatty acid methyl esters by gas chromatography was carried out using a 15 m×0.5 mm Supelcowax column (Supelco, Bellefonte, Pa.) with flame ionization detection. The initial column temperature of 160° C. was held for 0.5 min, then raised at 20° C./min to 190° C. and thereafter at 5° C./min to 215° C. This final temperature was held for 10 min.

The 22:5, ω-6 fatty acid was prepared from lipids of the marine organism Schizochytrium. Schizochytrium lipids (100 mg) were dissolved in 1 mL tetrahydrofuran and converted to fatty acid methyl esters as described (Miquel and Browse, J. Biol. Chem. 267:1502–1509, 1992). The 22:5 methyl ester was separated from other components by chromatography on silica gel G plates that had been dipped in a solution of 5% $AgNO_3$+0.01% rhodamine B in acetonitrile using a solvent containing hexane:diethyl ether 40:60 (v/v). Fatty acid methyl ester bands were visualized under ultraviolet light and the 22:5 (second band from the bottom of each plate) was scraped into a screw-cap tube. Water (4 mL), methanol (10 mL) and chloroform (10 mL) were added to the silica gel. The mixture was filtered through glass wool and the silica gel rinsed with 5 mL of chloroform:methanol:water (1:1:0.1, v/v/v). The combined filtrate was separated into two phases by addition of 4 mL $H_2O$. The 22:5-methyl ester was recovered with the lower phase, reduced to dryness under a stream of nitrogen, redissolved in hexane, and stored under argon at −20° C. To prepare the sodium soap of 22:5, a sample of the hexane solution was dried-in a screw-cap tube under a stream of nitrogen, redissolved in 0.3 mL of 1 M KOH in 95% aqueous methanol, sealed under argon, and heated to 80° C. for 90 minutes. After cooling, the preparation was diluted with 2 mL of water and extracted with 2 mL of hexane to remove non-saponifiable lipids. After removal of the hexane phase, the aqueous solution was titrated to pH 10 using 0.1 M HCl. Fatty acid methyl esters from a sample of this solution were analyzed by gas chromatography to confirm the identity of the 22:5 potassium soap and to calculate the concentration of the soap.

There was extensive incorporation of the exogenous 22:5, ω-6 fatty acid into phosphatidylcholine and phosphatidylethanolamine, which are the major phospholipids of the endoplasmic reticulum and other extrachloroplast membranes of plant cells. Phosphatidylcholine is the major lipid substrate for the plant 18:1 and 18:2 desaturases (Miquel and Browse, J. Biol. Chem. 278:1502–1509, 1992; Browse et al., J. Biol. Chem. 268:16345–16351, 1993). In wild-type leaves, the peak corresponding to Δ4,7,10,13, 16–22:5 accounted for approximately 2–4% of the total fatty acids in phosphatidylcholine, but there was no detectable conversion of this fatty acid to the ω-3 unsaturated Δ4,7, 10,13,16,19–22:6. By contrast, in leaves of plants expressing the fat-1 cDNA, the peak corresponding to 22:5, ω-6 was substantially replaced by a peak corresponding to the expected ω-3 unsaturated product, Δ4,7,10,13,16,19–22:6. Data for three independent experiments are shown in Table 3. The identity of the 22:6, ω-3 product was confirmed by GC-MS as described above to show that the retention time, molecular ion peak (m/z=342), and fragmentation pattern of the fatty acid isolated from fat-1 transgenic plants corresponded to those of genuine Δ4,7,10,13,16,19–22:6.

These results demonstrate that the FAT-1 protein, expressed in a heterologous host from a fat-1 cDNA, efficiently converts Δ4,7,10,13,16–22:5 to Δ4,7,10,13,16, 19–22:6.

We also supplied 22:5, ω-6 (0.025% w/v as the potassium soap in aqueous solution containing 1% v/v dimethylsulfoxide) to live Caenorhabditis elegans growing in liquid culture. The C. elegans incorporated the exogenous fatty acid into phospholipids and converted it to 22:6, ω-3.

TABLE 3

Metabolism of 22:5, ω-6 fatty acid in wild-type Arabidopsis and transgenic Arabidopsis of line #9.7 expressing a fat-1 cDNA. Results are the amounts of 22:5, ω-6 and 22:6, ω-3 in phosphatidylcholine expressed as a percentage of the total fatty acids in this lipid.

|  |  | 22:5 | 22:6 | Total | % conversion* |
|---|---|---|---|---|---|
| Experiment 1 |  |  |  |  |  |
| wild-type | water control | 0.00 | 0.00 | 0.00 | — |
| fat-1 | water control | 0.00 | 0.00 | 0.00 | — |
| wild-type | +22:5 | 3.25 | 0.00 | 3.25 | 0 |
| fat-1 | +22:5 | 1.35 | 1.82 | 3.17 | 57 |

TABLE 3-continued

Metabolism of 22:5, ω-6 fatty acid in wild-type Arabidopsis and transgenic Arabidopsis of line #9.7 expressing a fat-1 cDNA. Results are the amounts of 22:5, ω-6 and 22:6, ω-3 in phosphatidylcholine expressed as a percentage of the total fatty acids in this lipid.

|  |  | 22:5 | 22:6 | Total | % conversion* |
|---|---|---|---|---|---|
| Experiment 2 | | | | | |
| wild-type | +22:5 | 2.67 | 0.00 | 2.67 | 0 |
| fat-1 | +22:5 | 0.57 | 2.31 | 2.88 | 80 |
| Experiment 3 | | | | | |
| wild-type | +22:5 | 2.09 | 0.00 | 2.09 | 0 |
| fat-1 | | 0.36 | 1.67 | 2.03 | 82 |

*Percent conversion is calculated as 22:6/(22:5 + 22:6).

Example 5
Expression of FAT-1 in Yeast

A fat-1 cDNA was incorporated into the pYX232 yeast expression vector (Novagen Inc., 597 Science Dr., Madison, Wis. 53711) in a sense orientation at the multicloning site (to create plasmid pYX232:fat-1) so that it could be expressed in yeast (*Saccharomyces cerevisiae*) cells under control of the triosephosphate isomerase promoter. The fat-1 vector construct was transformed into yeast cells (strain YRP685), in which an ω-6 fatty acyl substrate, Δ9,12–18:2, was available. Gas chromatography analysis of yeast cells derived from this transformation experiment contained approximately 1% of their total fatty acids as 18:3 compared with less than 0.5% in control cells that did not contain pYX232:fat-1. This increase in accumulation of 18:3 indicates that the fat-1 cDNA encodes a product that is able to act as an ω-3 fatty acid desaturase in yeast. One can readily increase the level of ω-3 desaturation in yeast cells using the same fat-1 coding sequence but employing, for example, different combinations of well-known promoters and yeast strains.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

---

What is claimed is:

1. A host cell transformed with a recombinant polynucleotide encoding a polypeptide, wherein the polypeptide has an amino acid sequence as set forth as SEQ ID NO: 2, and wherein the polypeptide desaturates an ω-6 fatty acid to a corresponding ω-3 fatty acid.

2. A host cell transformed with a recombinant polynucleotide encoding a polypeptide, wherein the recombinant polynucleotide comprises a nucleotide sequence as set forth as SEQ ID NO: 1, and wherein the polypeptide desaturates an ω-6 fatty acid to a corresponding ω-3 fatty acid.

3. A method of desaturating an ω-6 fatty acid to a corresponding ω-3 fatty acid, comprising:

providing a host cell transformed with a recombinant polynucleotide encoding a polypeptide, wherein the polypeptide has a sequence as set forth as SEQ ID NO: 2; and growing the host cell under conditions under which the polypeptide is expressed and desaturates an ω-6 fatty acid to produce a corresponding ω-3 fatty acid.

4. A method of desaturating an ω-6 fatty acid to a corresponding ω-3 fatty acid, comprising:

providing a host cell transformed with a recombinant polynucleotide encoding a polypeptide, wherein the polynucleotide has a sequence as set forth as SEQ ID No: 1; and growing the host cell under conditions under which the polypeptide is expressed and desaturates an ω-6 fatty acid to produce a corresponding ω-3 fatty acid.

* * * * *

SEQUENCE LISTING (1) GENERAL INFORMATION:

(iii) NUMBER OF SEQUENCES:  2

(2) INFORMATION FOR SEQ ID NO:1:

(i) SEQUENCE CHARACTERISTICS:
      (A) LENGTH:  1391 base pairs
      (B) TYPE:  nucleic acid
      (C) STRANDEDNESS:  double stranded
      (D) TOPOLOGY:  linear (xi) SEQUENCE DESCRIPTION:  SEQ ID NO:1:

```
CAAGTTTGAG GT                                                      12

ATG GTC GCT CAT TCC TCA GAA GGG TTA TCC GCC ACG GCT CCG GTC        57
Met Val Ala His Ser Ser Glu Gly Leu Ser Ala Thr Ala Pro Val
5               10                  15

ACC GGC GGA GAT GTT CTG GTT GAT GCT CGT GCA TCT CTT GAA GAA       102
Thr Gly Gly Asp Val Leu Val Asp Ala Arg Ala Ser Leu Glu Glu
20              25                  30

AAG GAG GCT CCA CGT GAT GTG AAT GCA AAC ACT AAA CAG GCC ACC       147
Lys Glu Ala Pro Arg Asp Val Asn Ala Asn Thr Lys Gln Ala Thr
35              40                  45

ACT GAA GAG CCA CGC ATC CAA TTA CCA ACT GTG GAT GCT TTC CGT       192
Thr Glu Glu Pro Arg Ile Gln Leu Pro Thr Val Asp Ala Phe Arg
50              55                  60

CGT GCA ATT CCA GCA CAC TGT TTC GAA AGA GAT CTC GTT AAA TCA       237
Arg Ala Ile Pro Ala His Cys Phe Glu Arg Asp Leu Val Lys Ser
65              70                  75

ATC AGA TAT TTG GTG CAA GAC TTT GCG GCA CTC ACA ATT CTC TAC       282
Ile Arg Tyr Leu Val Gln Asp Phe Ala Ala Leu Thr Ile Leu Tyr
80              85                  90

TTT GCT CTT CCA GCT TTT GAG TAC TTT GGA TTG TTT GGT TAC TTG       327
Phe Ala Leu Pro Ala Phe Glu Tyr Phe Gly Leu Phe Gly Tyr Leu
95              100                 105
```

```
GTT TGG AAC ATT TTT ATG GGA GTT TTT GGA TTC GCG TTG TTC GTC        372
Val Trp Asn Ile Phe Met Gly Val Phe Gly Phe Ala Leu Phe Val
110             115                 120

GTT GGA CAC GAT TGT CTT CAT GGA TCA TTC TCT GAT AAT CAG AAT        417
Val Gly His Asp Cys Leu His Gly Ser Phe Ser Asp Asn Gln Asn
125             130                 135

CTC AAT GAT TTC ATT GGA CAT ATC GCC TTC TCA CCA CTC TTC TCT        462
Leu Asn Asp Phe Ile Gly His Ile Ala Phe Ser Pro Leu Phe Ser
140             145                 150

CCA TAC TTC CCA TGG CAG AAA AGT CAC AAG CTT CAC CAT GCT TTC        507
Pro Tyr Phe Pro Trp Gln Lys Ser His Lys Leu His His Ala Phe
155             160                 165

ACC AAC CAC ATT GAC AAA GAT CAT GGA CAC GTG TGG ATT CAG GAT        552
Thr Asn His Ile Asp Lys Asp His Gly His Val Trp Ile Gln Asp
170             175                 180

AAG GAT TGG GAA GCA ATG CCA TCA TGG AAA AGA TGG TTC AAT CCA        597
Lys Asp Trp Glu Ala Met Pro Ser Trp Lys Arg Trp Phe Asn Pro
185             190                 195

ATT CCA TTC TCT GGA TGG CTT AAA TGG TTC CCA GTG TAC ACT TTA        642
Ile Pro Phe Ser Gly Trp Leu Lys Trp Phe Pro Val Tyr Thr Leu
200             205                 210

TTC GGT TTC TGT GAT GGA TCT CAC TTC TGG CCA TAC TCT TCA CTT        687
Phe Gly Phe Cys Asp Gly Ser His Phe Trp Pro Tyr Ser Ser Leu
215             220                 225

TTT GTT CGT AAC TCT GAC CGT GTT CAA TGT GTA ATC TCT GGA ATC        732
Phe Val Arg Asn Ser Asp Arg Val Gln Cys Val Ile Ser Gly Ile
230             235                 240

TGT TGC TGT GTG TGT GCA TAT ATT GCT CTA ACA ATT GCT GGA TCA        777
Cys Cys Cys Val Cys Ala Tyr Ile Ala Leu Thr Ile Ala Gly Ser
245             250                 255

TAT TCC AAT TGG TTC TGG TAC TAT TGG GTT CCA CTT TCT TTC TTC        822
Tyr Ser Asn Trp Phe Trp Tyr Tyr Trp Val Pro Leu Ser Phe Phe
260             265                 270

GGA TTG ATG CTC GTC ATT GTT ACC TAT TTG CAA CAT GTC GAT GAT        867
Gly Leu Met Leu Val Ile Val Thr Tyr Leu Gln His Val Asp Asp
275             280                 285

GTC GCT GAG GTG TAC GAG GCT GAT GAA TGG AGC TTC GTC CGT GGA        912
Val Ala Glu Val Tyr Glu Ala Asp Glu Trp Ser Phe Val Arg Gly
290             295                 300

CAA ACC CAA ACC ATC GAT CGT TAC TAT GGA CTC GGA TTG GAC ACA        957
Gln Thr Gln Thr Ile Asp Arg Tyr Tyr Gly Leu Gly Leu Asp Thr
305             310                 315

ACG ATG CAC CAT ATC ACA GAC GGA CAC GTT GCC CAT CAC TTC TTC        1002
Thr Met His His Ile Thr Asp Gly His Val Ala His His Phe Phe
320             325                 330

AAC AAA ATC CCA CAT TAC CAT CTC ATC GAA GCA ACC GAA GGT GTC        1047
Asn Lys Ile Pro His Tyr His Leu Ile Glu Ala Thr Glu Gly Val
335             340                 345

AAA AAG GTC TTG GAG CCG TTG TCC GAC ACC CAA TAC GGG TAC AAA        1092
Lys Lys Val Leu Glu Pro Leu Ser Asp Thr Gln Tyr Gly Tyr Lys
350             355                 360

TCT CAA GTG AAC TAC GAT TTC TTT GCC CGT TTC CTG TGG TTC AAC        1137
Ser Gln Val Asn Tyr Asp Phe Phe Ala Arg Phe Leu Trp Phe Asn
365             370                 375

TAC AAG CTC GAC TAT CTC GTT CAC AAG ACC GCC GGA ATC ATG CAA        1182
Tyr Lys Leu Asp Tyr Leu Val His Lys Thr Ala Gly Ile Met Gln
380             385                 390

TTC CGA ACA ACT CTC GAG GAG AAG GCA AAG GCC AAG TAA                1221
Phe Arg Thr Thr Leu Glu Glu Lys Ala Lys Ala Lys
```

```
                     395              400
AAGAATATCC CGTGCCGTTC TAGAGTACAA CAACAACTTC TGCGTTTTCA          1271

CCGGTTTTGC TCTAATTGCA ATTTTTCTTT GTTCTATATA TATTTTTTG           1321

CTTTTTAATT TTATTCTCTC TAAAAAACTT CTACTTTTCA GTGCGTTGAA          1371

TGCATAAAGC CATAACTCTT                                            1391
```

(2) INFORMATION FOR SEQ ID NO: 2:

(i) SEQUENCE CHARACTERISTICS:
        (A) LENGTH: 402 amino acid residues
        (B) TYPE: amino acid
        (C) STRANDEDNESS: single stranded
        (D) TOPOLOGY: linear (xi) SEQUENCE DESCRIPTION: SEQ ID NO:2:

```
Met Val Ala His Ser Ser Glu Gly Leu Ser Ala Thr Ala Pro Val
                  5                  10                  15

Thr Gly Gly Asp Val Leu Val Asp Ala Arg Ala Ser Leu Glu Glu
 20                  25                  30

Lys Glu Ala Pro Arg Asp Val Asn Ala Asn Thr Lys Gln Ala Thr
 35                  40                  45

Thr Glu Glu Pro Arg Ile Gln Leu Pro Thr Val Asp Ala Phe Arg
 50                  55                  60

Arg Ala Ile Pro Ala His Cys Phe Glu Arg Asp Leu Val Lys Ser
 65                  70                  75

Ile Arg Tyr Leu Val Gln Asp Phe Ala Ala Leu Thr Ile Leu Tyr
 80                  85                  90

Phe Ala Leu Pro Ala Phe Glu Tyr Phe Gly Leu Phe Gly Tyr Leu
 95                 100                 105

Val Trp Asn Ile Phe Met Gly Val Phe Gly Phe Ala Leu Phe Val
110                 115                 120

Val Gly His Asp Cys Leu His Gly Ser Phe Ser Asp Asn Gln Asn
125                 130                 135

Leu Asn Asp Phe Ile Gly His Ile Ala Phe Ser Pro Leu Phe Ser
140                 145                 150

Pro Tyr Phe Pro Trp Gln Lys Ser His Lys Leu His His Ala Phe
155                 160                 165

Thr Asn His Ile Asp Lys Asp His Gly His Val Trp Ile Gln Asp
170                 175                 180

Lys Asp Trp Glu Ala Met Pro Ser Trp Lys Arg Trp Phe Asn Pro
185                 190                 195

Ile Pro Phe Ser Gly Trp Leu Lys Trp Phe Pro Val Tyr Thr Leu
200                 205                 210

Phe Gly Phe Cys Asp Gly Ser His Phe Trp Pro Tyr Ser Ser Leu
215                 220                 225

Phe Val Arg Asn Ser Asp Arg Val Gln Cys Val Ile Ser Gly Ile
230                 235                 240

Cys Cys Cys Val Cys Ala Tyr Ile Ala Leu Thr Ile Ala Gly Ser
245                 250                 255

Tyr Ser Asn Trp Phe Trp Tyr Tyr Trp Val Pro Leu Ser Phe Phe
260                 265                 270

Gly Leu Met Leu Val Ile Val Thr Tyr Leu Gln His Val Asp Asp
275                 280                 285

Val Ala Glu Val Tyr Glu Ala Asp Glu Trp Ser Phe Val Arg Gly
290                 295                 300
```

-continued

```
Gln Thr Gln Thr Ile Asp Arg Tyr Tyr Gly Leu Gly Leu Asp Thr
305                 310                 315

Thr Met His His Ile Thr Asp Gly His Val Ala His His Phe Phe
320                 325                 330

Asn Lys Ile Pro His Tyr His Leu Ile Glu Ala Thr Glu Gly Val
335                 340                 345

Lys Lys Val Leu Glu Pro Leu Ser Asp Thr Gln Tyr Gly Tyr Lys
350                 355                 360

Ser Gln Val Asn Tyr Asp Phe Phe Ala Arg Phe Leu Trp Phe Asn
365                 370                 375

Tyr Lys Leu Asp Tyr Leu Val His Lys Thr Ala Gly Ile Met Gln
380                 385                 390

Phe Arg Thr Thr Leu Glu Glu Lys Ala Lys Ala Lys
395                 400
```